United States Patent
Lezer

(10) Patent No.: US 6,419,912 B1
(45) Date of Patent: Jul. 16, 2002

(54) HYPOALLERGENIC MAKE-UP OR CARE COMPOSITION COMPRISING A CROSSLINKED ORGANOPOLYSILOXANE COMPRISING AN OXYALKYLENE GROUP, AND ITS USES

(75) Inventor: Nathalie Jager Lezer, Bourg la Reine (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/538,509

(22) Filed: Mar. 30, 2000

(30) Foreign Application Priority Data

Mar. 30, 1999 (FR) .............................. 99 03969

(51) Int. Cl.$^7$ .............................................. A61K 31/74
(52) U.S. Cl. ...................... 424/78.03; 424/401; 424/63; 424/61; 424/59; 424/65; 424/64; 424/69; 424/70.1
(58) Field of Search .......................... 424/401, 63, 61, 424/59, 65, 64, 69, 70.1, 78.03; 524/27

(56) References Cited

U.S. PATENT DOCUMENTS 5,412,004 A * 5/1995 Tachibana et al. ............ 524/27
5,599,533 A    2/1997 Stepniewski et al.
5,811,487 A * 9/1998 Schulz, Jr. et al. ......... 524/862

FOREIGN PATENT DOCUMENTS

| EP | 0 295 886 | 12/1988 |
|---|---|---|
| EP | 0 501 791 | 9/1992 |
| EP | 0 706 789 | 4/1996 |
| EP | 0 893 467 | 1/1999 |
| JP | 11-021227 | 1/1999 |

* cited by examiner

*Primary Examiner*—Thurman K. Page
*Assistant Examiner*—Liliana Di Nola-Baron
(74) *Attorney, Agent, or Firm*—Oblon, Spivak, McClelland, Maier & Neustadt, P.C.

(57) ABSTRACT

A hypoallergenic composition for making up or caring for keratinous substances which comprises an aqueous phase dispersed in a liquid fatty phase by means of particles of crosslinked elastomeric solid organopolysiloxane comprising at least one oxyalkylene group and in particular an oxyethylene group, the said composition additionally being devoid of cosurfactant. The invention also relates to the use of these particles of elastomeric solid organopolysiloxane in a hypoallergenic and fresh cosmetic composition or for the manufacture of a hypoallergenic and fresh care, treatment or make-up composition, comprising an aqueous phase dispersed in a liquid fatty phase.

26 Claims, No Drawings

HYPOALLERGENIC MAKE-UP OR CARE COMPOSITION COMPRISING A CROSSLINKED ORGANOPOLYSILOXANE COMPRISING AN OXYALKYLENE GROUP, AND ITS USES

BACKGROUND OF THE INVENTION

Field of the Invention

The present invention relates to a composition for caring for and/or making up the skin and/or lips of human beings exhibiting both hypoallergenic and freshness properties. This composition is in particular a care cream, an eyeliner, a face powder, an eyeshadow, a foundation or alternatively an antisun product, a deodorant cream or a conditioner. It is provided in the form of a more or less thick, water-in-oil, oil-in-water-in-oil or water-in-oil-in-water emulsion. The invention also relates to the use of particles of a specific organopolysiloxane in a hypoallergenic composition for the skin or lips.

Description of the Background

Water-in-oil (W/O) emulsions exhibit the disadvantage, with respect to an oil-in-water (O/W) emulsion, of comprising only a small amount of water and therefore contributing only a small degree of freshness to the skin or lips to which they are applied.

Furthermore, they often confer a greasy and glistening appearance on the skin, which does not allow them to be used or allows them to be used with difficulty in hot and humid environments and/or by users with greasy skin.

Furthermore, in order to disperse or emulsify the aqueous phase in the liquid fatty phase, it is necessary to use a certain amount of surfactants, which surfactants are often irritating and poorly tolerated by people with sensitive skin and can even lead to allergenic reactions.

The need therefore remains for a nongreasy hypoallergenic composition at the same time exhibiting freshness properties.

SUMMARY OF THE INVENTION

The Inventor has found, surprisingly, that it is possible, by using specific crosslinked organopolysiloxanes as sole emulsifier, to form hypoallergenic compositions comprising a W/O emulsion which are devoid of surfactant and which comprise a large amount of water.

Although there exist compounds of the crosslinked organopolysiloxane type which disperse in an aqueous medium, such as, for example, the compounds of KSG 20 or KSG 21 type sold by Shin Etsu, the specific chemical structure of which (cf. U.S. Pat. No. 5,236,986 of Shin Etsu) is responsible for the dispersion in an aqueous medium (presence of polar groups conferring surfactant properties on them), these compounds, in contrast to those of the composition of the invention, are not capable of emulsifying a large amount of water (namely, up to 70% by weight of water). They therefore do not allow freshness to be contributed, like the organopolysiloxanes of the composition according to the present invention.

A specific subject-matter of the present invention is a composition for caring for or making up the skin or lips of human beings which overcomes the various disadvantages mentioned above and which provides a make-up or a care product which exhibits improved cosmetic properties with respect to those of the products of the prior art, in particular properties of freshness, of slip and of non-drying of the skin and lips, without contributing greasiness, and which additionally exhibits properties of hypoallergenicity and of non-irritation of the skin and lips.

The invention applies not only to products for making up the lips and skin of human beings but also to products for caring for and/or treating human lips and skin, including the scalp.

Thus, the present invention provides a hypoallergenic composition suitable as a make up or care agent for keratinous substances, comprising:

an aqueous phase, a liquid fatty phase, and particles of a crosslinked solid elastomeric organopolysiloxane comprising at least one oxyalkylene group, wherein the aqueous phase is dispersed in the liquid fatty phase, and the composition is devoid of cosurfactant.

The present invention also provides a method of preparing the inventive composition, comprising mixing the aqueous phase, liquid fatty phase, and particles of a crosslinked solid elastomeric organopolysiloxane comprising at least one oxyalkylene group.

The present invention also provides a method of treating skin, comprising applying the inventive composition to the skin.

A more complete appreciation of the invention and many of the attendant advantages thereof will be readily obtained as the same becomes better understood by reference to the following detailed description.

DETAILED DESCRIPTION OF THE INVENTION

The term "cosurfactant" refers any amphiphilic compound capable of emulsifying an aqueous phase in a liquid fatty phase which has an HLB (hydrophile/lipophile balance) value of less than 6. The composition according to the invention preferably comprises less than 0.01% of cosurfactant.

The invention also relates to the use of particles of crosslinked elastomeric solid organopolysiloxane comprising at least one oxyalkylenated and more especially oxyethylenated group in a hypoallergenic and fresh care or make-up composition or for the manufacture of a hypoallergenic and fresh care or make-up composition or for sensitive and/or reactive skin and/or lips. In particular, this composition comprises an aqueous phase dispersion in a liquid fatty phase.

The term "elastomeric" refers to a flexible and deformable material having viscoelastic properties and in particular the consistency of a sponge or of a flexible sphere. Its modulus of elasticity is such that this material is resistant to deformation and has a limited ability to expand and to contract. This material is capable of returning to its original shape after it has been stretched. This elastomer is formed of polymeric chains of high molecular weight, the mobility of which is limited by a uniform network of crosslinking points.

The organopolysiloxanes of the composition of the invention comprise one or more oxyalkylene and in particular oxyethylene (OE) groups, for example from 1 to 40 oxyalkylene units, preferably from 1 to 20 and better still from 12 to 20 oxyalkylene units, which can form polyoxyalkylene and in particular polyoxyethylene chains. These groups can be pendant, at the chain end or intended to connect two parts of the silicone structure. The silicon atoms carrying these groups, indeed even these chains, advantageously number from 1 to 10 and better still from 1 to 6.

Although the invention relates more especially to organopolysiloxanes comprising oxyethylene groups(s) (namely, only comprising oxyethylene groups as oxyalkylene groups), it can also relate to organopolysiloxanes comprising oxypropylene group(s), that is to say only comprising oxypropylene groups as oxyalkylene groups. The organopolysiloxanes can also comprise both one or more oxyethylene (OE) group(s), for example 1 to 20, and one or more oxypropylene (OP) group(s), for example 0 to 20; these organopolysiloxanes are also known as organopolysiloxanes comprising alkylethoxy-propylene group(s). The number of oxyethylene groups is preferably greater than the number of oxypropylene groups.

Furthermore, the silicone structure forming the polymeric backbone of the organopolysiloxane comprising oxyalkylene group(s) is advantageously a polydimethylsiloxane (PDMS) structure, a portion of the methyl groups of which is optionally substituted by $C_2$ to $C_{30}$ and preferably $C_8$ to $C_{24}$ and better still from $C_{10}$ to $C_{20}$ alkyl groups or phenyl groups, either at the chain end or at pendant positions.

Furthermore, the organopolysiloxane comprising oxyalkylene group(s) can comprise one or more silicone backbone(s) connected to one another by one or more oxyalkylene and preferably oxyethylene groups as defined above or by one or more alkylene groups, the alkylene group number ranging from 1 to 20 and preferably from 1 to 10. The organopolysiloxane preferably comprises at least two polymeric backbones connected to one another.

The silicone backbone or backbones of these organopolysiloxanes of the composition according to the invention advantageously comprise from 26 to 80 silicon atoms.

The elastomeric organopolysiloxanes of the composition of the invention exhibit a notable ability to thicken a liquid fatty phase and to emulsify an aqueous phase in a liquid fatty phase; they swell in the liquid fatty phase. They do not dry out the skin and contribute good cosmetic properties, in particular of softness, of freshness, of nongreasiness and of ease of application. These novel elastomers result in compositions which are comfortable on application, spread well, are soft and are not sticky to the touch. These cosmetic properties are due, on the one hand, to the texture of the organopolysiloxanes and, on the other hand, to their properties, comparable to those of microsponges, of trapping oily media and in particular those of the composition and those secreted by the skin.

The composition of the invention can be provided in the form of a paste, solid or more or less fluid cream. It can be a more or less fluid water-in-oil emulsion which is optionally solid, a multiple emulsion, and in particular a water-in-oil-in-water or oil-in-water-in-oil emulsion. This composition can have the appearance of a lotion, of a cream or of a cast product and can even be provided in the form of an aerosol.

The amount of water is preferably greater than 70% of the total weight of the composition, for the purpose of contributing maximum freshness.

The composition according to the invention is stable, that is to say that it does not separate at room temperature for at least two months. The elastomeric organopolysiloxanes in accordance with the invention are partially or completely crosslinked and have a three-dimensional structure. When included in an oily phase, they are converted, according to the level of oily phase used, from a product with a spongy appearance, when they are used in the presence of small contents of oily phase, to a homogeneous gel, in the presence of larger amounts of oily phase. The gelling of the oily phase by these elastomers can be complete or partial.

The elastomers of the invention are provided in the form of a powder or gel which is emulsified comprising an elastomeric organopolysiloxane with a three-dimensional structure dispersed in a liquid fatty phase.

The term "liquid fatty phase" or alternatively "oily phase" refers any non-aqueous substance or mixture of non-aqueous substances which is liquid at room temperature (25° C.) and atmospheric pressure (760 mm of Hg).

The elastomeric organopolysiloxanes according to the invention can be chosen from the crosslinked polymers obtained by an addition and crosslinking reaction in a non-aqueous medium, in the presence of a catalyst, in particular of the platinum type, of at least:

(a) one first organopolysiloxane (i) having at least two vinyl groups in the α,'Ω-position of the silicone chain; and (b) one second organopolysiloxane (ii) having at least one hydrogen atom bonded to a silicon atom per molecule and at least one oxyalkylene, in particular oxyethylene, group.

The organopolysiloxane (i) is chosen in particular from polydimethylsiloxanes (PDMSs) and is more especially an α,ω-dimethylvinylpolydimethylsiloxane. The organopolysiloxane (ii) is chosen in particular from polydimethylsiloxanes comprising one or more hydrogen atom(s), each bonded to a silicon atom, and one or more oxyethylene groups and optionally one or more oxypropylene groups bonded to a silicon atom via an alkylene radical having from 1 to 22 carbon atoms.

The silicone chains of the first and second organopolysiloxanes (i) and (ii) optionally comprise $C_1$ to $C_6$ alkyl pendant chains and/or aryl chains.

The elastomeric organopolysiloxanes of the composition according to the invention are advantageously provided in the form of an anhydrous gel. This gel can be obtained as follows:

(a) mixing the first organopolysiloxane (i) and the second organopolysiloxane (ii);

(b) adding the oily phase to the mixture of stage (a); and (c) polymerizing the first organopolysiloxane (i) and the second organopolysiloxane (ii) in the oily phase in the presence of a catalyst, preferably a platinum catalyst.

The oily phase used during the manufacture of the anhydrous gel comprises one or more oils which are liquid at room temperature (25° C.) chosen from hydrocarbonaceous oils and/or silicone oils. The oily phase is advantageously a silicone liquid phase comprising one or more oils chosen from PDMSs with a linear or cyclic chain which are liquid at room temperature, optionally comprising a pendant alkyl or aryl chain or an alkyl or aryl chain at the chain end, the alkyl chain having from 1 to 6 carbon atoms.

The term "hydrocarbonaceous oils" refers to oils containing essentially hydrogen and carbon atoms and in particular alkyl, alkyl or alkenyl chains like alkane or alkene oils. These oils may contain, also, one or several ester, ether, hydro or carbocyclic groups and mixtures thereof.

The organopolysiloxanes of the invention are obtained in particular according to the procedure of Examples 3, 4 and 8 of the document U.S. Pat. No. 5,412,004 and of the examples of the document U.S. Pat. No. 5,811,487. The organopolysiloxane of Example 3 of U.S. Pat. No. 5,412,004 is preferably used. The disclosure of these patents is incorporated herein by reference.

The product of Example 3 of the document U.S. Pat. No. 5,412,004 is provided in the form of a pasty gel comprising approximately 33% by weight of crosslinked organopolysiloxane comprising oxyethylene group(s) and approximately 67% of 6 cSt PDMS. The organopolysiloxane comprises approximately 18% of the total weight of the polymer of ethylene oxide. The elastomeric gel of the present invention has a plastic shear thinning behavior with a viscosity, at low shear in the region of $10^{-3}$ to $10^{-4}$ s$^{-1}$, ranging from $2\times10^6$P to $4\times10^6$P and a dynamic viscosity ranging from 15 to 50P for a shear rate of 200 s$^{-1}$, measured with an RS 75 (Haake) controlled-stress rheometer at 25° C. in cone/plate geometry; characteristics of the cone: diameter of 20 mm, angle of 1° and gap of 40 μm. The organopolysiloxane of the invention additionally has a viscoelastic behavior of 1 HZ with a dominant elastic nature at low values of the shear stress defined as follows: 800 Pa<$G^*_{plate}$<2500 Pa with $\delta_{plate}$ in the region of 10°, $G^*_{plate}$ representing the consistency and $\delta_{plate}$ representing the elasticity. It exhibits a flash point of approximately 170° C. at atmospheric pressure.

The dynamic viscosity of the elastomeric gel of Example 3 of U.S. Pat. No. 5,412,004 is 45P for a shear rate of 200 s$^{-1}$.

This elastomeric organopolysiloxane gel is preferably present in the composition at a level of 0.5 to 99% and better still of 3 to 75%, which corresponds to a level of polymer, as active material, of 0.1 to 33% by weight and better still of 1 to 25%. The elastomeric gel of the invention is, in addition, stable at room temperature at least 4 months, without any degradation.

In particular, the particles of elastomeric organopolysiloxane (as active material) have a size ranging from 0.1 to 500 μm and better still from 3 to 200 μm, and preferably from 3 to 50 μm. These particles can be spherical, flat or amorphous with preferably a spherical shape.

The elastomeric organopolysiloxane of the invention is in particular a surfactant with an HLB (Hydrophilic-Lipophilic Balance) of approximately 2.5. It is therefore perfectly suited to the manufacture of a stable water-in-oil emulsion or of a stable oil-in-water-in-oil or water-in-oil-in-water emulsion. The emulsion is preferably a simple water-in-oil emulsion, in order to decrease even further the risks of reactions on the part of the skin and lips.

This elastomeric organopolysiloxane gel can be used in combination with fatty substances which are liquid at room temperature, waxes or gums which are solid at room temperature, or pasty fatty substances of animal, vegetable, mineral or synthetic origin and their mixtures.

There is no restriction on the additional fatty phase and it can comprise products which are liquid at room temperature, such as silicone, fluorinated, fluorosilicone or optionally partially silicone-comprising hydrocarbonaceous oils. These oils can be volatile at room temperature and atmospheric pressure. The term "volatile oil" is understood to mean in particular an oil capable of evaporating, in less than one hour, on contact with the skin or lips which has in particular a non-zero vapour pressure, especially ranging from $10^{-3}$ to 300 mm of Hg (at room temperature and atmospheric pressure) and preferably greater than 0.3 mm of Hg.

These oils can represent from 1 to 80% of the total weight of the composition, preferably from 1 to 50% and better still from 1 to 30%. Mention may in particular be made, as oils which can be used in the composition of the invention, of:

- hydrocarbonaceous oils of animal origin, such as perhydrosqualene;
- vegetable hydrocarbonaceous oils, such as liquid fatty acid triglycerides, for example sunflower, maize, soybean, gourd, grape seed, sesame, hazelnut, apricot, macadamia, castor or avocado oils, or triglycerides of caprylic/capric acids, such as those sold by Stearineries Dubois or those sold under the names Miglyol 810, 812 and 818 by Dynamit Nobel;
- oils of formula $R^1COOR^2$, in which $R^1$ represents the residue of a higher fatty acid comprising from 7 to 19 carbon atoms and $R^2$ represents a branched hydrocarbonaceous chain comprising from 3 to 20 carbon atoms, such as, for example, purcellin oil, isopropyl myristate, or octanoates, decanoates or ricinoleates of alcohols or of polyalcohols;
- linear or branched hydrocarbons of mineral or synthetic origin, such as volatile or non-volatile liquid paraffins and their derivatives, liquid petrolatum, polydecenes or hydrogenated polyisobutene, such as parleam;
- synthetic ethers of formula $R^3OR^4$, in which $R^3$ is a $C_3$ to $C_{19}$ alkyl radical and $R^4$ a $C_3$ to $C_{20}$ alkyl radical;
- fatty alcohols, such as octyldodecanol or oleyl alcohol;
- fluorinated oils which are partially hydrocarbonaceous and/or silicone-comprising, such as perfluoropolyesters;
- silicone oils, such as polymethylsiloxanes with a linear or cyclic silicone chain which are liquid or pasty at room temperature, phenyl dimethicones, phenyl trimethicones, polymethylphenylsiloxanes, and alkylpolydimethylsiloxanes with a $C_2$ to $C_{20}$ alkyl chain;
- their mixtures.

The gel formed of organopolysiloxane comprising oxyethylene group(s) makes it possible to structure these oils in the form of a novel texture of "custard tart" type which is devoid of oily gelling agent which would interfere with the soft/silky and pleasant feel of the composition.

The composition according to the invention can advantageously comprise at least one wax chosen from hydrocarbonaceous, fluorinated or silicone waxes and their mixtures which can be solid or semisolid (in the form of a paste) at room temperature. These waxes can be of vegetable, mineral, animal and/or synthetic origin. These waxes exhibit in particular a starting melting temperature of greater than 25° C. and better still of greater than 45° C. at atmospheric pressure.

According to the invention, a wax is a lipophilic fatty substance which is solid at room temperature, with reversible solid/liquid state changes, which has a starting melting temperature which can range up to 200° C. and which exhibits, in the solid state, an anisotropic crystalline organization. On bringing the wax to its melting temperature, it is possible to make it miscible with the liquid fatty phase and to form a microscopically homogeneous mixture and then, on returning the temperature of the mixture to room temperature, crystallization of the wax in the liquid fatty phase of the mixture is obtained.

The silicone waxes can be waxes comprising a silicone structure and units with one or more pendant alkyl or alkoxy chains and/or one or more alkyl or alkoxy chains at the end of the silicone structure, these chains being linear or branched and comprising from 10 to 45 carbon atoms. These waxes are known respectively as alkyl dimethicones and alkoxy dimethicones. Furthermore, these alkyl chains can comprise one or more ester functional groups.

Mention may be made, as other waxes which can be used in the invention, of waxes of animal origin, such as lanolin or beeswax, waxes of vegetable origin, such as carnauba or candelilla wax, waxes of mineral origin, for example paraffin wax, lignite wax, microcrystalline waxes, ceresin or ozokerite, or synthetic waxes, such as polyethylene waxes.

These fatty substances can be chosen variously by a person skilled in the art in order to prepare a composition having the desired properties, for example of consistency or of texture.

In particular, the presence of waxes makes it possible to provide good mechanical strength, in particular when the composition is provided in the form of a stick.

The composition can generally comprise from 0 to 50% of the total weight of the composition of wax and preferably from 5 to 30%.

The composition of the invention comprises a liquid aqueous phase comprising in particular water and water-miscible solvents in any proportion, such as polyols (glycerol, diglycerol or ethylene glycol), lower $C_2$ to $C_5$ monoalcohols, acetone and diacetone alcohol. The aqueous phase can represent from 5 to 75% of the total weight of the composition and better still from 5 to 60%.

The composition of the invention can additionally comprise any additive conventionally used in the field under consideration, such as water-soluble or fat-soluble dyes, antioxidants, essential oils, preservatives, cosmetic or dermatological active principles, fat-soluble polymers, in particular hydrocarbonaceous polymers, such as polyalkylenes, gelling agents for the aqueous phase, gelling agents for the fatty phase, fragrances or electrolytes, such as divalent or monovalent salts (NaCl, $MgCl_2$ or $MgSO_4$).

These additives can be present in the composition according to amounts commonly used, for example in a proportion of 0 to 20% of the total weight of the composition and better still of 0.1 to 10%. For the electrolytes, use is in particular made of at least 30 to 60 milliosmol.

The composition of the invention advantageously comprises, as additives, one or more gelling agents for the aqueous phase, namely compounds capable of giving the appearance of a gel to the composition and of thickening it. Mention may be made, among the gelling agents for the aqueous phase which can be used according to the invention, of: water-soluble cellulose gelling agents, such as hydroxyethylcellulose, methylcellulose, hydroxypropylcellulose, carboxyethylcellulose and carboxymethylcellulose; guar gum; quatemized guar gum; nonionic guar gums comprising $C_1$–$C_6$ hydroxyalkyl groups; xanthan, locust bean, scleroglucan, gellan, rhamsan or karoya gums; alginates, maltodextrin, starch and its derivatives, or hyaluronic acid and its salts; clays and in particular montmorillonites, hectorites or bentones, or laponites; polymers with a carboxyl group, such as crosslinked poly(acrylic acid)s which are at least partially neutralized, such as the "Carbopol" or "Carbomer" products from Goodrich (Carbomer 980, for example, neutralized with triethanolamine, abbreviated to TEA); poly(glyceryl (meth) acrylate) polymers; polyvinylpyrrolidone; poly(vinyl alcohol); crosslinked acrylamide polymers and copolymers; crosslinked methacryloyloxyethyltrimethylammonium chloride homopolymers; or associated polyurethanes.

According to the invention, the gelling agent for the aqueous phase is preferably chosen from xanthan gum, clays (bentone or laponite), associated polyurethanes, cellulose thickeners, in particular hydroxyethyl cellulose, and crosslinked poly(acrylic acid)s which are at least partially neutralized.

Of course, a person skilled in the art will take care to choose the optional supplementary additives and/or their amounts so that the advantageous properties of the composition according to the invention are not, or not substantially, detrimentally affected by the envisaged addition. In particular, these additives must not be harmful to the homogeneity, the stability, the comfort, the freshness and the hypoallergenicity of the composition of the invention.

The composition according to the invention can be provided in the form of a colored product, in particular for making up the skin, especially a foundation, a face powder, an eyeshadow, an eyeliner or a concealer stick, a product for making up the body (body painting), a make-up for the superficial body growths, such as a mascara or a nail varnish, or a make-up for the lips, such as a lipstick. They can also be provided in the uncolored form, optionally comprising cosmetic or dermatological active principles. It can then be used as a care base for the lips (lip balms, protecting the lips from the cold and/or the sun and/or the wind) or a fixing base to be applied to a conventional lipstick (the fixing base then forming a protective film on the film of rouge, which limits the transfer thereof).

The composition of the invention can also be provided in the form of a dermatological or cosmetic composition for treating or caring for the skin (including the scalp), keratinous fibers (hair, eyelashes or eyebrows), nails or lips or in the form of a composition for antisun protection or artificial tanning or in the form of a product for cleansing or removing make-up from the skin or keratinous fibers or a deodorant product.

Of course, the composition of the invention must be cosmetically or dermatologically acceptable, namely non-toxic and capable of being applied to the skin (including the inside of the eyelids) or lips of human beings.

Preferably, the composition of the invention can comprise a particulate phase which is generally present in a proportion of 0 to 60% of the total weight of the composition, preferably of 5 to 35%, and which can comprise pigments and/or pearlescent agents and/or fillers commonly used in cosmetic compositions.

The term "pigments" refers to white or colored and inorganic or organic particles, insoluble in the medium of the composition, intended to color and/or opacify the composition. The term "fillers" should be understood as meaning colorless or white, inorganic or synthetic and lamellar or non-lamellar particles. The term "pearlescent agents" should be understood as meaning iridescent particles produced in particular by certain molluscs in their shells or else synthesized. These fillers and pearlescent agents are used to modify the texture of the composition and the mattness/gloss effect.

The pigments can be present in the composition in a proportion of 0 to 60% of the weight of the final composition and preferably in a proportion of 4 to 25%. Mention may be made, as inorganic pigments which can be used in the invention, of titanium, zirconium or cerium oxides, as well as zinc, iron or chromium oxides and ferric blue. Mention may be made, among the organic pigments which can be used in the invention, of carbon black and barium, strontium, calcium or aluminium lakes. The pigments may or may not be coated.

The pearlescent agents can be present in the composition in a proportion of 0 to 20% of the total weight of the composition, preferably at a level of the order of 2 to 15%. Mention may be made, among the pearlescent agents which can be used in the invention, of mica covered with titanium oxide, with iron oxide, with natural pigment or bismuth oxychloride, such as colored titanium oxide-coated mica.

The fillers can be present in a proportion of 0 to 35% of the total weight of the composition, preferably 0 to 15%. Mention may in particular be made of talc, mica, silica, kaolin, powders formed of Nylon (in particular Orgasol) and of polyethylene, Teflon, starch, boron nitride, microspheres formed of copolymers, such as Expancel (Nobel Industrie)

or Polytrap (Dow Corning), silicone resin microbeads (Tospearl from Toshiba, for example) and fibers, for example polyamide fibers.

The organopolysiloxane comprising oxyethylene group(s) exhibits the advantage of finely dispersing the pigments and of thus conferring a homogeneous make-up. It additionally exhibits the advantage of outstandingly stabilizing the compositions of the invention.

The composition according to the invention can be manufactured under cold conditions or by heating one or more elastomeric organopolysiloxanes in the form of an anhydrous gel, addition or one or more pigments and/or of one or more other additives, optional addition of molten fatty substances (in particular brought to the highest melting temperature of the waxes), addition of the aqueous phase and then emulsification.

Another subject-matter of the invention is the use of particles of crosslinked elastomeric solid organopolysiloxane comprising at least one oxyalkylene group, in particular an oxyethylene group, in a hypoallergenic and fresh cosmetic composition or for the manufacture of a hypoallergenic and fresh treatment, make-up or care composition for the skin or lips, comprising an aqueous phase dispersed in a liquid fatty phase, the composition being suitable for a person having sensitive and/or reactive skin and/or lips.

Another subject-matter of the invention is a cosmetic process for increasing the contribution of freshness and of hypoallergenicity of a cosmetic composition comprising an aqueous phase dispersed in a liquid fatty phase which consists in emulsifying the aqueous phase in the liquid fatty phase using particles of a crosslinked elastomeric organopolysiloxane as they have been defined above.

EXAMPLES

Hydrocarbonaceous oils Having generally described this invention, a further understanding can be obtained by reference to certain specific examples which are provided herein for purposes of illustration only and are not intended to be limiting unless otherwise specified. The percentages are given by weight.

Example 1

| Preparation of a hypoallergenic foundation with a "custard tart" texture | |
|---|---|
| Fatty phase | |
| Silicone oil (PDMS 6 cSt) | 10% |
| Pigment | 10% |
| Modified silicone (Example 3 of U.S. Pat. No. 5,412,004) | 18% (5.7 as active material) |
| Aqueous phase | |
| Preservative | q.s. |
| Divalent salt | 0.4% |
| Water | q.s. for 100% |

Result:

A foundation with a gel texture of "custard tart" type is obtained which has high freshness on application, which has good hold over time and which is devoid of surfactant other than the elastomer and of coemulsifier.

Preparation:

The organopolysiloxane is swollen in the oil at room temperature, the pigments and aqueous phase are subsequently added and then the combined ingredients are mixed with stirring until the oily phase has been emulsified in the aqueous phase.

Example 2

| Preparation of a hypoallergenic care cream | |
|---|---|
| Fatty phase | |
| Modified silicone (Example 3 of U.S. Pat. No. 5,412,004) | 18% |
| Silicone oil (PDMS, 6 cSt) | 10% |
| Aqueous phase | |
| Preservative | q.s. |
| Divalent salt | 0.7% |
| Water | q.s. for 100% |

Result:

A non-greasy cream with a consistency of "dessert" type is obtained which is very fresh and which has good hold over time. This cream comprises more than 70% of water without addition of surfactant other than the elastomer or coemulsifier.

Preparation:

This composition is prepared as in Example 1.

Obviously, numerous modifications and variations of the present invention are possible in light of the above teachings. It is therefore to be understood that within the scope of the appended claims, the invention may be practiced otherwise than as specifically described herein.

This application is based on French Patent Application Serial No. 9903969, filed on Mar. 30, 1999, and incorporated herein by reference in its entirety.

What is claimed is:

1. A hypoallergenic composition suitable as a make up or care agent for keratinous substances, comprising:

an aqueous phase, a liquid fatty phase, particles of a crosslinked solid elastomeric organopolysiloxane comprising at least one oxyalkylene group, 4 to 60% by weight of a particulate phase containing pigments and/or pearlescent agents and/or fillers, and 30 to 60 milliosmol of electrolyte wherein the aqueous phase is dispersed in the liquid fatty phase, and the composition is devoid of cosurfactant.

2. The composition of claim 1, wherein the elastomeric organopolysiloxane comprises at least one oxyethylene group.

3. The composition of claim 1, wherein the oxyalkylene groups consist of oxyethylene groups.

4. The composition of claim 1, wherein the elastomeric organopolysiloxane is obtained by a process comprising:

reacting, in a non-aqueous medium and in the presence of a catalyst, (i) a first organopolysiloxane having at least two vinyl groups in the α,ω-position of the silicone chain per molecule and (ii) a second organopolysiloxane having at least one hydrogen atom bonded to a silicon atom per molecule and at least one oxyalkylene group.

5. The composition of claim 4, wherein (i) is selected from the group consisting of polydimethylsiloxanes.

6. The composition of claim 4, wherein (i) is an α,ω-dimethylvinyl-polydimethylsiloxane.

7. The composition of claim 4, wherein (ii) is selected from the group consisting of polydimethylsiloxanes comprising one or more hydrogen atoms and one or more oxyalkylene groups bonded to a silicon atom via an alkylene radical having from 1 to 22 carbon atoms.

8. The composition of claim 4, wherein the organopolysiloxane particles are in the form of an anhydrous gel obtained by a process comprising:
   (a) mixing (i) and (ii);
   (b) adding the liquid fatty phase to the mixture from (a); and
   (c) polymerizing (i) and (ii) in the liquid fatty phase in the presence of a platinum catalyst.

9. The composition of claim 1, wherein the organopolysiloxane particles are in the form of a gel having a viscoelastic behavior at 1 Hz of shear stress such as 800 Pa<$G^*_{plate}$<500 Pa, wherein with $G^*_{plate}$ represents the consistency and with a $\delta_{plate}$ in the region of 10°, wherein $\delta_{plate}$ is the elasticity.

10. The composition of claim 1, wherein the organopolysiloxane particles have a size from 3 to 200 μm.

11. The composition of claim 1, wherein the liquid fatty phase comprises one or more liquid hydrocarbonaceous and/or silicone oils.

12. The composition of claim 1, wherein the composition comprises at least one fatty substance selected from the group consisting of volatile or nonvolatile oils, waxes, gums and pasty fatty substances of animal, vegetable, mineral or synthetic origin, and mixtures thereof.

13. The composition of claim 1, wherein the elastomeric organopolysiloxane represents from 0.1 to 33% of the total weight of the composition.

14. The composition of claim 1, wherein the aqueous phase represents from 5 to 75% of the total weight of the composition.

15. The composition of claim 1, wherein the liquid fatty phase represents from 1 to 80% of the total weight of the composition.

16. The composition of claim 1, containing 5 to 35% by weight of the particulate phase.

17. The composition of claim 1, further comprising at least one cosmetic or dermatological active agent.

18. The composition of claim 1, which is in the form of a simple emulsion.

19. The composition of claim 1, which is in the form of a foundation, face powder or eyeshadow composition, of a concealer product, of a lipstick, of an eyeliner, of a mascara, of a product for making up the body, of a care base or of a fixing base for the lips, of a dermatological or care product for the skin or keratinous fibers, of a composition for antisun protection or artificial tanning, of a product for cleansing the skin or keratinous fibers, or a deodorant cream.

20. The composition of claim 1, further comprising at least one component selected from the group consisting of preservatives, fragrances, and gelling agents.

21. A method of preparing the composition of claim 1, comprising mixing the aqueous phase, liquid fatty phase, particles of a crosslinked solid elastomeric organopolysiloxane comprising at least one oxyalkylene group, the particulate phase, and the electrolyte.

22. A method of treating skin, comprising applying the composition of claim 1 to the skin.

23. The composition of claim 1, which contains the pigments.

24. The composition of claim 1, which contains the pearlescent agents.

25. The composition of claim 1, which contains the fillers.

26. A method of preparing a hypoallergenic make-up composition suitable for making-up human skin or lips, wherein the composition comprises an aqueous phase and a liquid fatty phase, comprising:
   dispersing said aqueous phase in said liquid fatty phase with the aid of particles of crosslinked solid elastomeric organopolysiloxane having at least one oxyalkylene group and without a co-surfactant,
   adding 4 to 60% by weight of a particulate phase containing pigments and/or pearlescent agents and/or fillers; and
   adding from 30 to 60 milliosmol of electrolyte.

* * * * *